United States Patent [19]

Green et al.

[11] Patent Number: 4,752,024
[45] Date of Patent: Jun. 21, 1988

[54] SURGICAL FASTENER AND SURGICAL STAPLING APPARATUS

[76] Inventors: David T. Green, 251 Wolpit Ave., Norwalk, Conn. 06581; Herbert W. Korthoff, 110 Old Belden Hill Rd., Wilton, Conn. 06897

[21] Appl. No.: 920,581

[22] Filed: Oct. 17, 1986

[51] Int. Cl.⁴ ............................................. A61B 17/00
[52] U.S. Cl. ...................................... 227/19; 227/DIG. 1
[58] Field of Search ..................... 128/334 R, 334 C; 227/19, DIG. 1, 15; 411/450, 456, 457, 461, 462, 463, 469, 908

[56] References Cited

U.S. PATENT DOCUMENTS

| | | | |
|---|---|---|---|
| 3,494,533 | 2/1970 | Green et al. | 227/19 |
| 4,198,982 | 4/1980 | Fortner et al. | 227/DIG. 1 |
| 4,304,236 | 12/1981 | Conta et al. | 227/DIG. 1 |
| 4,351,466 | 9/1982 | Noiles | 227/DIG. 1 |
| 4,423,730 | 1/1984 | Gabbay | 128/334 R |
| 4,473,077 | 9/1984 | Noiles et al. | 227/DIG. 1 |
| 4,476,863 | 10/1984 | Kanshin et al. | 128/334 C |
| 4,488,523 | 12/1984 | Shichman | 227/DIG. 1 |
| 4,505,272 | 3/1985 | Utyamyshev et al. | 128/334 C X |
| 4,505,414 | 3/1985 | Filipi | 227/DIG. 1 |
| 4,567,891 | 2/1986 | Kanshin et al. | 128/334 R X |
| 4,598,712 | 7/1986 | Rebuffat et al. | 128/334 R X |
| 4,603,693 | 8/1986 | Conta et al. | 227/DIG. 1 |
| 4,681,108 | 7/1987 | Rosaii et al. | 128/334 R |

Primary Examiner—Paul A. Bell

[57] ABSTRACT

The two-part surgical fastener is composed of an annular stapling part having projecting prongs and annular retaining board having an annular gap which receives the prongs. Barbs on the prongs serve to abut against a retaining ring on the retaining part to maintain a fixed relationship between the parts for stapling purposes. The anvil assembly on which the retaining part of the fastener is mounted as fingers which can be collapsed radially inwardly after stapling to permit ease of removal.

14 Claims, 13 Drawing Sheets

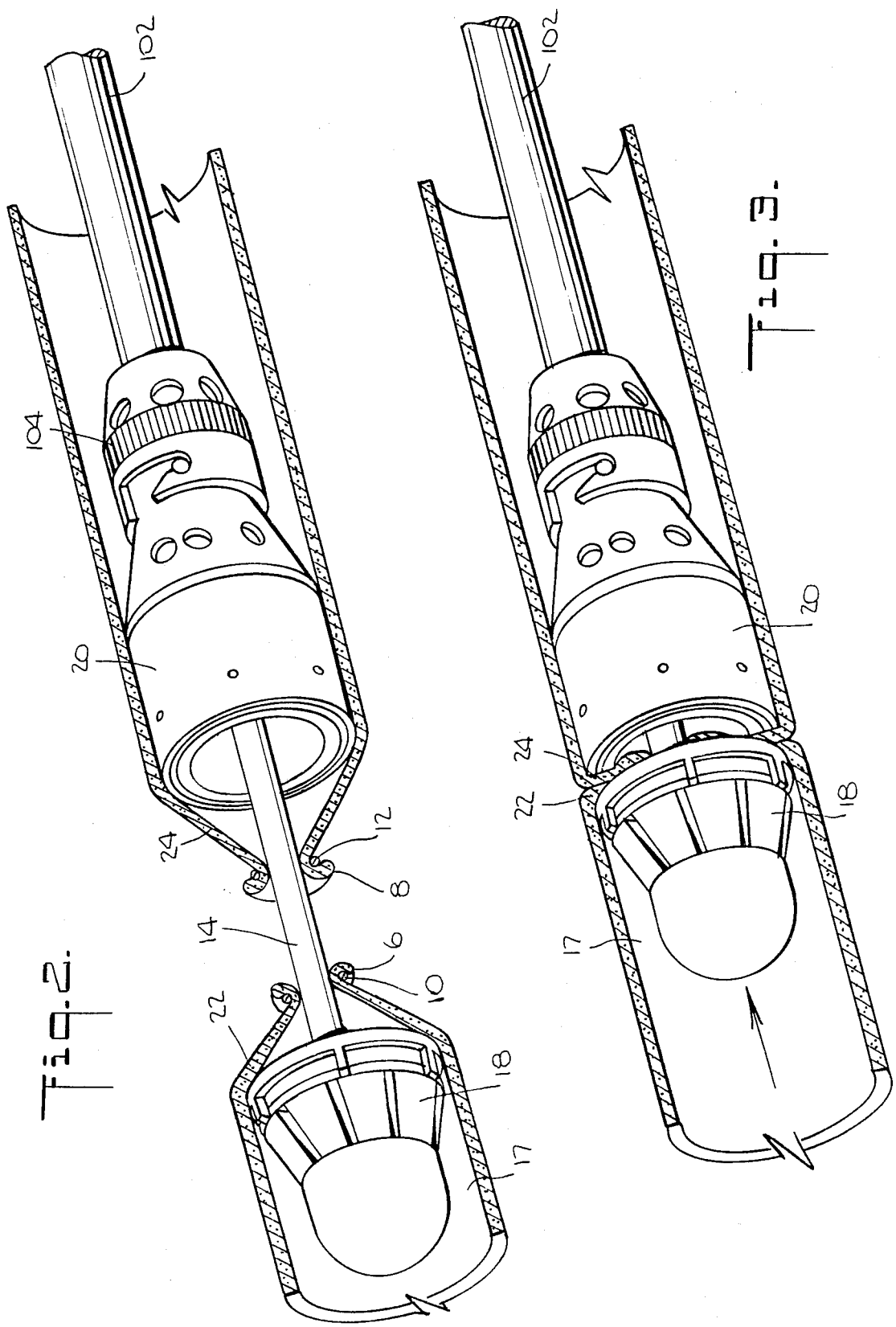

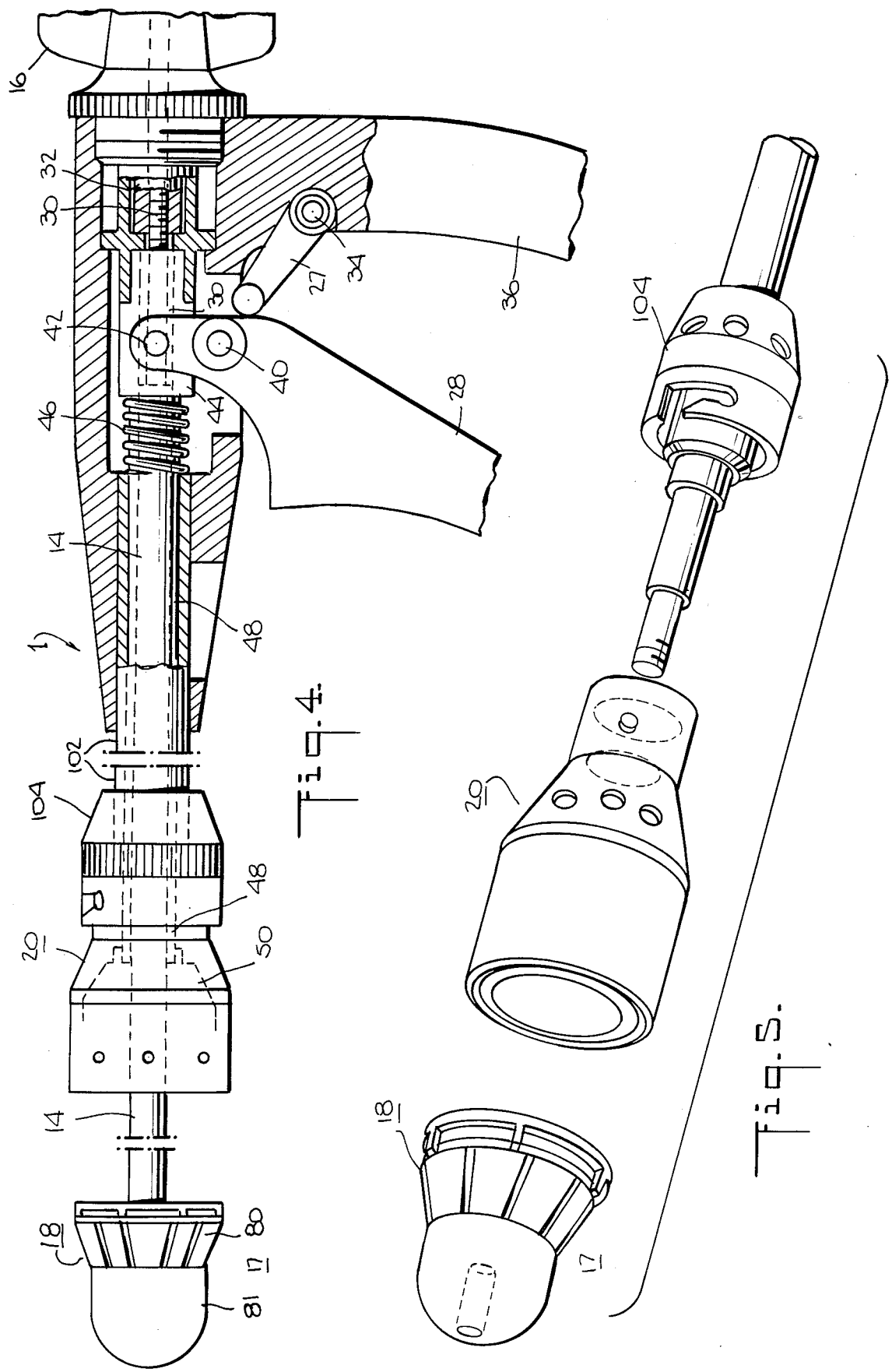

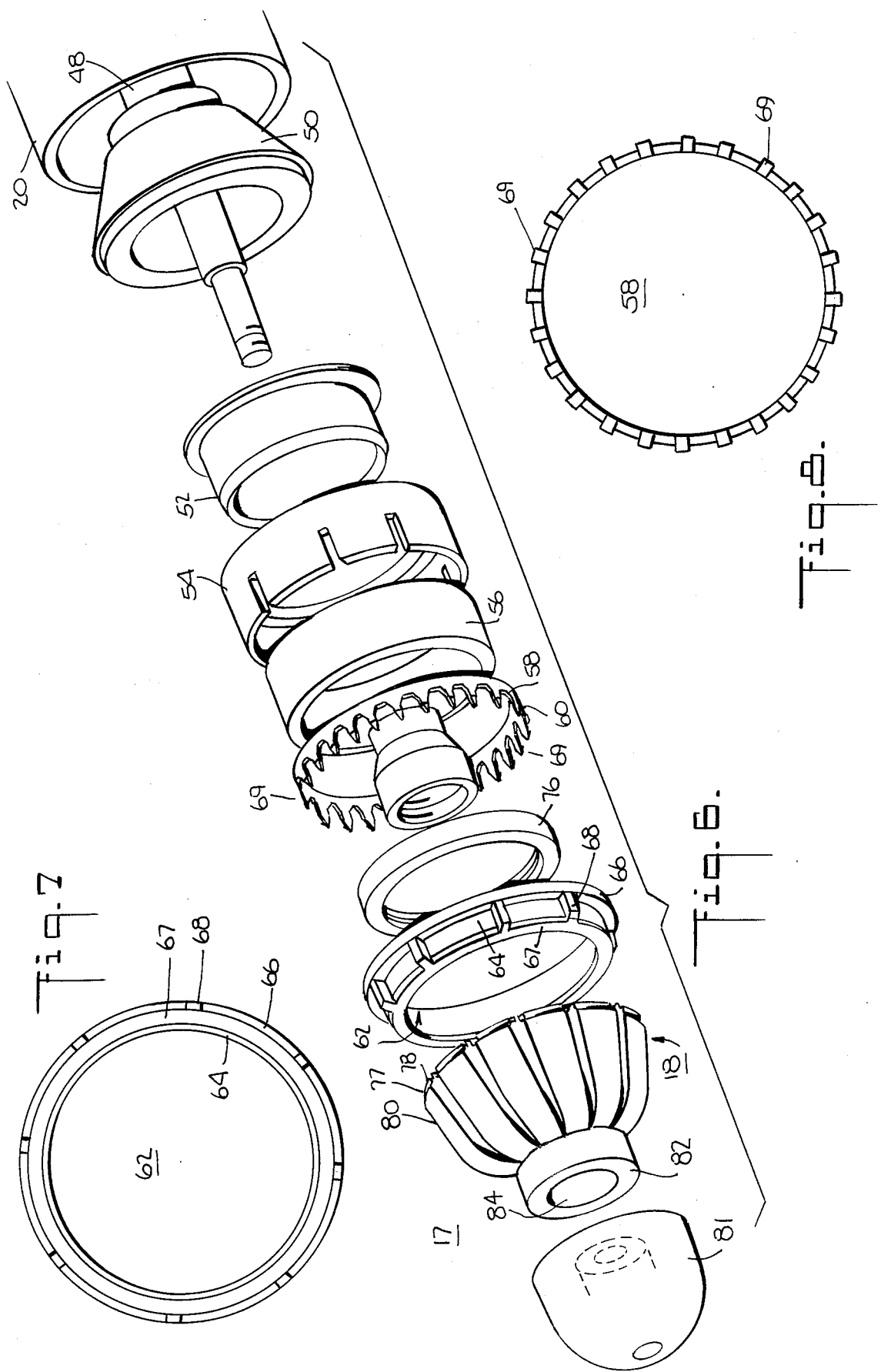

SURGICAL FASTENER AND SURGICAL STAPLING APPARATUS

This invention relates to a surgical fastener and to a surgical stapling apparatus.

Heretofore, various types of surgical stapling devices have been known wherein a stapling function takes place at a location which is relatively remote from the location at which the stapling device is held and actuated by an operator. For example linear closure surgical stapler devices are described in U.S. Pat. No. 3,494,533 and circular anastomosis surgical stapler devices are described in U.S. Pat. Nos. 4,304,236; 4,351,466; 4,473,077 and 4,488,523 as well as U.S. Pat. Nos. De. 273,041 and De. 271,944. Typically, the stapling devices described in these patents operate by placing tissue to be stapled in a clamped manner between an anvil assembly and a fastener holding assembly, both of which are located at the distal end of the instrument. The clamped tissue is stapled by driving one or more fasteners from the holding assembly so that the ends of the fasteners pass through the tissue and are formed properly by contact with the anvil assembly. The forces required to operate the instrument are applied by the operator of the instrument to one or more actuator elements located at or near the proximal end of the instrument. The distal and proximal portions of the instrument are joined by a longitudinal connecting shaft structure along which the actuating forces and motions are transmitted to the distal operation elements. This type of construction, including relatively widely spaced distal and proximal portions, may be employed for any of several reasons, such as the relative inaccessibility of the tissue to be stapled, the need for good visibility of the tissue during stapling, and the like.

These known types of surgical stapler devices generally use a plurality of small and discrete fasteners requiring precise registration with the anvil assembly to ensure that proper fastener formation occurs during the stapling operation.

Accordingly, it is an object of the invention to provide a unitary surgical fastener having a multiplicity of fastening points.

It is another object of the invention to eliminate the need for a plurality of precisely registered small and discrete fasteners in anastomosis stapling devices.

It is another object of the invention to provide a surgical stapler which can be easily and quickly installed in tissue by a surgical stapling apparatus.

It is another object of the invention to provide a surgical stapling apparatus with an anvil head capable of functioning with a unitary surgical fastener.

It is another object of the invention to eliminate the need for a high degree of rotational accuracy in the registration of a fastener holder relative to an anvil assembly in an anastomosis stapling device.

Briefly, the invention provides a surgical fastener which is comprised of an annular stapling part having a plurality of axially extending circumferentially spaced prongs each of which has a sharp tip for piercing tissue. In addition, the fastener has an annular retaining part with an annular gap for receiving the prongs of the stapling part. In addition, catch means are provided for holding the prongs in the retaining part in order to clamp pierced tissue therebetween. For example, the catch means may include a radially extending barb on at least one of the prongs and a retaining ring on the retaining part for butting of each barb thereon.

The retaining ring may also include a cylindrical guide wall about the retaining ring in order to define an annular gap to receive the prongs of the stapling part. Suitable means are also provided for securing the guide wall to the retaining ring.

The invention also provides an anvil assembly for the mounting of the surgical fastener. The anvil assembly includes a plurality of radiating fingers which extend angularly of a longitudinal axis, an annular cutting block which is removably mounted on the fingers for engagement with an annular knife blade and means for biasing the fingers radially inwardly of the block in order to permit movement of the fingers radially inwardly in response to removal of the cutting block from the fingers. In one embodiment, the fingers are integral with a central hub and are resiliently deformable while the means for biasing the fingers inwardly constitutes an anvil head having an internal wall receiving the anvil with the fingers abutting the wall and a retainer which is movably mounted within the anvil head and anvil in order to abut the hub and tension the resilient fingers radially inwardly. In another embodiment, the anvil head has an annular recess while each finger is separately mounted within the recess. In this embodiment, means for biasing the fingers includes an axially movable retainer ring concentrically within the fingers and mounted on the anvil head and a circular head in order to bias the fingers onto the retainer ring. In addition, each finger is provided with a recess so as to receive the retainer ring after axial movement of the ring in order to permit inward radial movement of the fingers under the action of the circular spring.

The invention also provides a surgical stapling apparatus which is comprised of a central shaft, an anvil assembly mounted on the distal end of the shaft and a surgical fastener holding assembly mounted on the shaft for relative movement with the anvil assembly to releaseably retain two ends of tubular tissue therebetween. In this regard, the anvil assembly includes a plurality of radiating fingers extending angularly outwardly of the shaft, an annular cutting block removably mounted on the fingers and means for biasing the fingers radially inwardly of the block. The holding assembly includes an annular knife blade coaxially opposite the cutting block for severing tissue disposed therebetween. This blade also has an edge for penetrating and holding the block thereon whereby upon movement of the holding assembly and the anvil assembly from each other, the block is removed from the fingers to permit the fingers to move radially inwardly for passage through a stapled seam between the two ends of the tissue.

The invention also provides a method of stapling the tubular ends of a pair of vessels together which includes the steps of clamping the tubular ends of the vessels between an anvil assembly and a surgical fastener holding assembly, driving an annular stapling part through the clamped ends of the tissue into an annular retaining part removably supported on the anvil assembly and severing the clamped ends on a circular cutting line disposed radially within the stapling part. In addition, the method includes the steps of moving the anvil assembly away from the stapled ends of the tissue to withdraw the anvil assembly from the annular retaining part, thereafter, collapsing the anvil assembly radially inwardly of the retaining part and the cutting line and then withdrawing the stapling apparatus from the stapled-together vessels.

These and other objects and advantages of the invention will become more apparent from the following detailed description taken in conjunction with the accompanying drawings wherein:

FIG. 2 illustrates a perspective view of the distal end of the stapling apparatus prior to fastening;

FIG. 3 illustrates a view similar to FIG. 2 of the distal end of the stapling apparatus during a stapling operation;

FIG. 4 illustrates a part sectional side view of the apparatus of FIG. 1;

FIG. 5 illustrates an exploded view of the distal end of the apparatus of FIG. 1;

FIG. 6 illustrates an exploded view of a surgical fastener, anvil assembly and holding assembly in accordance with the invention;

FIG. 7 illustrates a front view of an annular retaining part in accordance with the invention;

FIG. 8 illustrates a front view of an annular stapling part in accordance with the invention;

FIG. 9 illustrates an exploded view of the retaining part and stapling part in accordance with the invention;

FIG. 10 illustrates side views of the retaining part and stapling part of FIG. 9;

Figure 1:
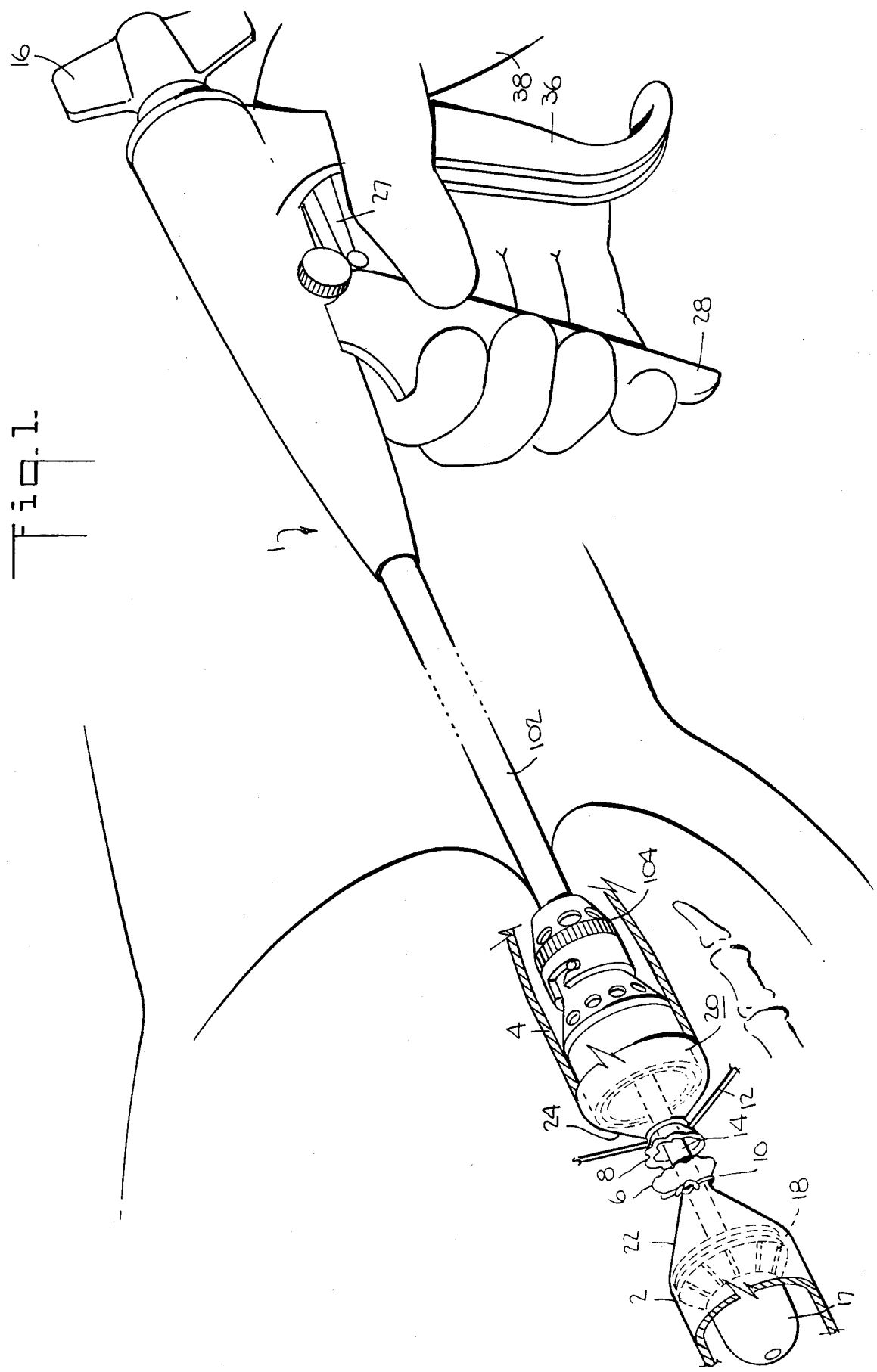
FIG. 1 illustrates a perspective view of a surgical stapling apparatus donstructed in accordance with the invention in place within an intestine.

Referring to FIGS. 1 and 4, the surgical stapling apparatus 1 is used, for example for the stapling of two ends 2, 4 of an intestine wherein a section of the intestine has been surgically removed between cut ends 6, 8. As indicated in FIG. 1, the cut ends 6, 8 of the intestine are generally tied with suture material 10, 12 with conventional purse-string suturing being used.

The stapling apparatus 1 includes a shaft 14 and a hand screw 16 which is articulated to the shaft 14 in order to move the shaft 14. As indicated in FIG. 4, the apparatus 1 includes an anvil assembly 17 which is mounted on a distal end of the shaft 14 and includes an anvil 18 which faces a surgical fastener holding assembly 20 which is also mounted on the shaft 14 for relative movement with the anvil assembly 17 to maintain the two ends of the intestine areas 22, 24 therebetween.

Referring to FIG. 4, the shaft 14 is provided with a screwthread 30 at the proximal end which mates in an internally threaded sleeve extension 32 of the hand screw 16. The sleeve extension 32 is secured to the hand screw 16 so that both turn together and thus the rotation of the hand screw 16 causes longitudinal movement of the shaft 14. By tightening the hand screw 16, the anvil assembly can be moved towards the holding assembly 20 so that the tissue can be clamped therebetween with proper spacing between the anvil assembly 17 and the holding assembly 20. Calibration means (not shown) may be provided to ensure proper spacing, for example as described in U.S. Pat. No. 4,473,077.

The apparatus 1 is also provided with a handle 36 and a trigger 28 which is pivotally mounted on a pivot pin 40 secured in the housing of the apparatus 1. A safety latch 27 is also pivotally mounted on a pivot pin 34 on the handle 36 in order to prevent pivoting of the trigger 28. In addition, the trigger 28 is articulated in known manner, for example via a pusher 42 to a slider 44 disposed about the shaft 14. This slider 44 abuts a compression spring 46 in order to apply a biasing force on a tube 48 concentric of the sleeve 14 in order to move the tube 48 distally upon actuation of the trigger 28. The tube 48, in turn, cooperates with an actuator 50 in order to perform a stapling operation.

Referring to FIGS. 4 and 5, the shaft 14 has a threaded distal end on which the anvil assembly 17 is mounted in threaded manner. In addition, a bayonet mount 104 is secured, in known manner on the tube 48. In this regard, the holding assembly 20 includes a sleeve at the proximal end which carries a pin for fitting into the bayonet connection of the mount 104. As indicated in FIG. 4, a sheath 102 is provided over the central part of the instrument and has a tubular portion 53 fitting within the bayonet mount 104 (see FIG. 12).

Referring to FIGS. 2 and 3, when the apparatus is initially put in place, the cut ends 6, 8 of the body tissue are drawn in about the shaft 14 with the anvil assembly 17 in a spaced condition relative to the holding assembly 20. During stapling, the anvil assembly 17 is drawn against the holding assembly 20 so as to clamp the ends of the tissue between the anvil assembly 17 and the holding assembly 20 (see FIG. 3).

Figure 12:
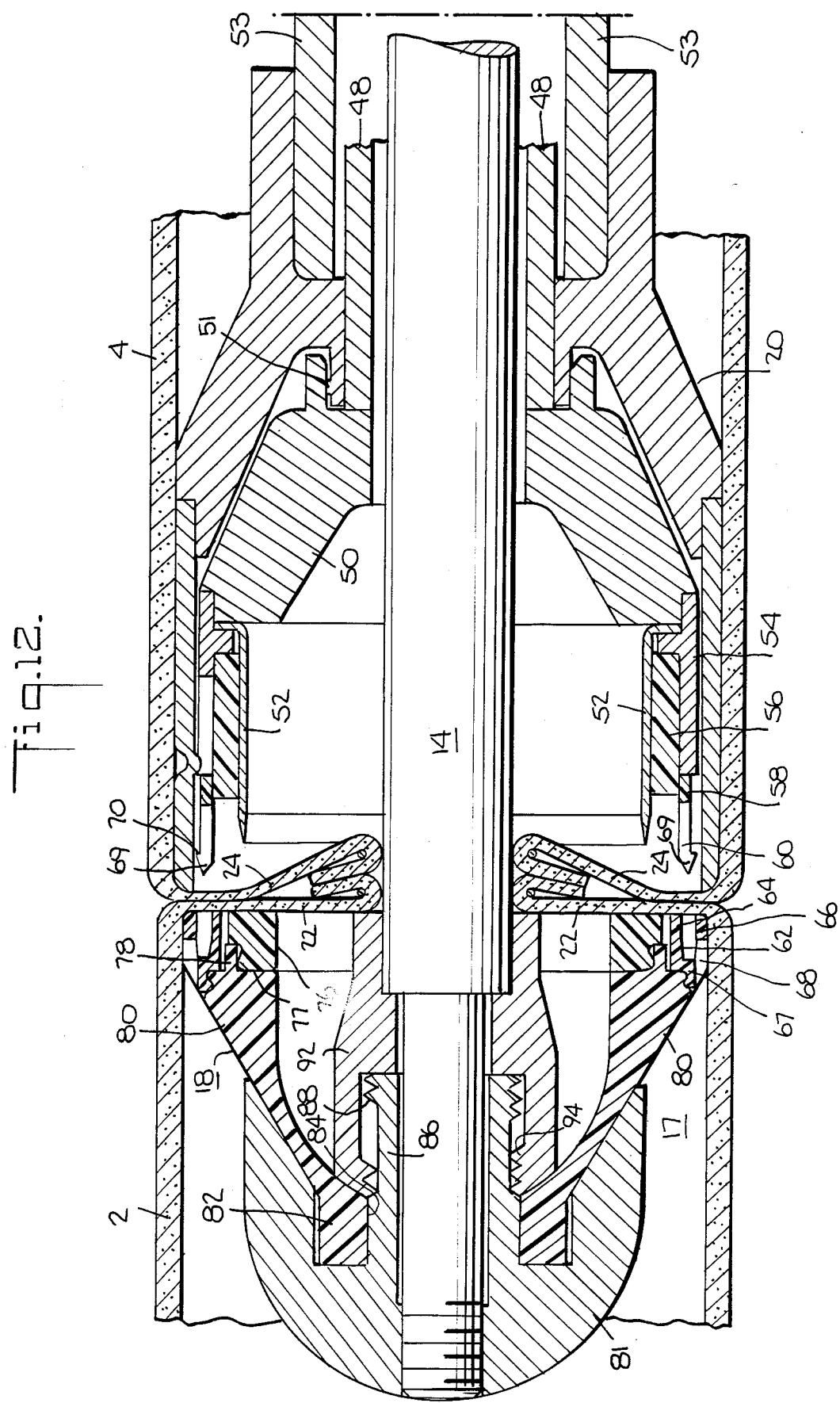
FIG. 12 illustrates a cross sectional view of the stapling components of the apparatus during an initial phase of stapling.

Referring to FIGS. 6 and 12, the actuator means includes an actuator 50 which is abutted against the distal end of the tube 48 and is disposed within the holding assembly 20. In this respect, the holding assembly is provided with a pad 51 which frictionally retains the actuator 50 in place until the actuator 50 is driven clear of the pad 51 by the tube 48. The actuator 50 carries an annular push ring 54 as well as an annular blade or scalpel 52 which is retained between the actuator 50 and push ring 54. In addition, a plastic spacer ring 56 is concentrically disposed between the push ring 54 and the annular scalpel 52. As indicated in FIG. 6, the push ring 54 is provided with a plurality of circumferentially disposed slots at the distal end.

An annular stapling part 58 is mounted about the spacer ring 56 and against the push ring 54 (see FIG. 12) and has a plurality of axially extending circumferentially spaced prongs 60.

The anvil 18 is made of resilient material and has a plurality of radiating fingers 80 extending angularly outwardly from a central hub 82 concentrically disposed about the longitudinal axis of the shaft 14. In this regard, the anvil 18 is made of one piece with several fingers 80. As indicated in FIG. 6, the anvil 18 has a somewhat frustum-like shape with the cylindrical hub 82 at the distal end. In addition, each finger 80 tapers in both thickness and width from the free end to the hub 82. In addition, the free end of each finger 80 has an extension 78 which forms a basal ridge as well as an annular reaction surface 77 within the extension 78.

An annular cutting block 76 is removably mounted within the outer ends of the fingers 80. That is, the cutting block 76 abuts against the reaction surfaces 77 of the fingers 80 within the extension 78. As indicated in FIG. 12, the cutting block 76 is aligned with the annular scalpel 52 and is made of a material so as to be penetrated by the cutting edge of the scalpel 52. The cutting block 76 is also shaped so as to be fitted into and about the extensions 78 in a slide fit manner.

An annular retaining part 62 is also mounted at the free ends of the fingers 80 of the anvil 18. As indicated, the retaining part 62 includes an inner cylindrical guide wall 64 and an outer retaining ring 66 which are concentrically disposed relative to each other to define an annular gap for receiving the prongs 60. Suitable means in the form of posts 68 (FIG. 8) are provided to secure the retainin ring 66 to the cylindrical wall 64. An annular flange 67 is also provided between the posts 68 and the guide wall 64 (FIG. 7).

Figures 9, 10:
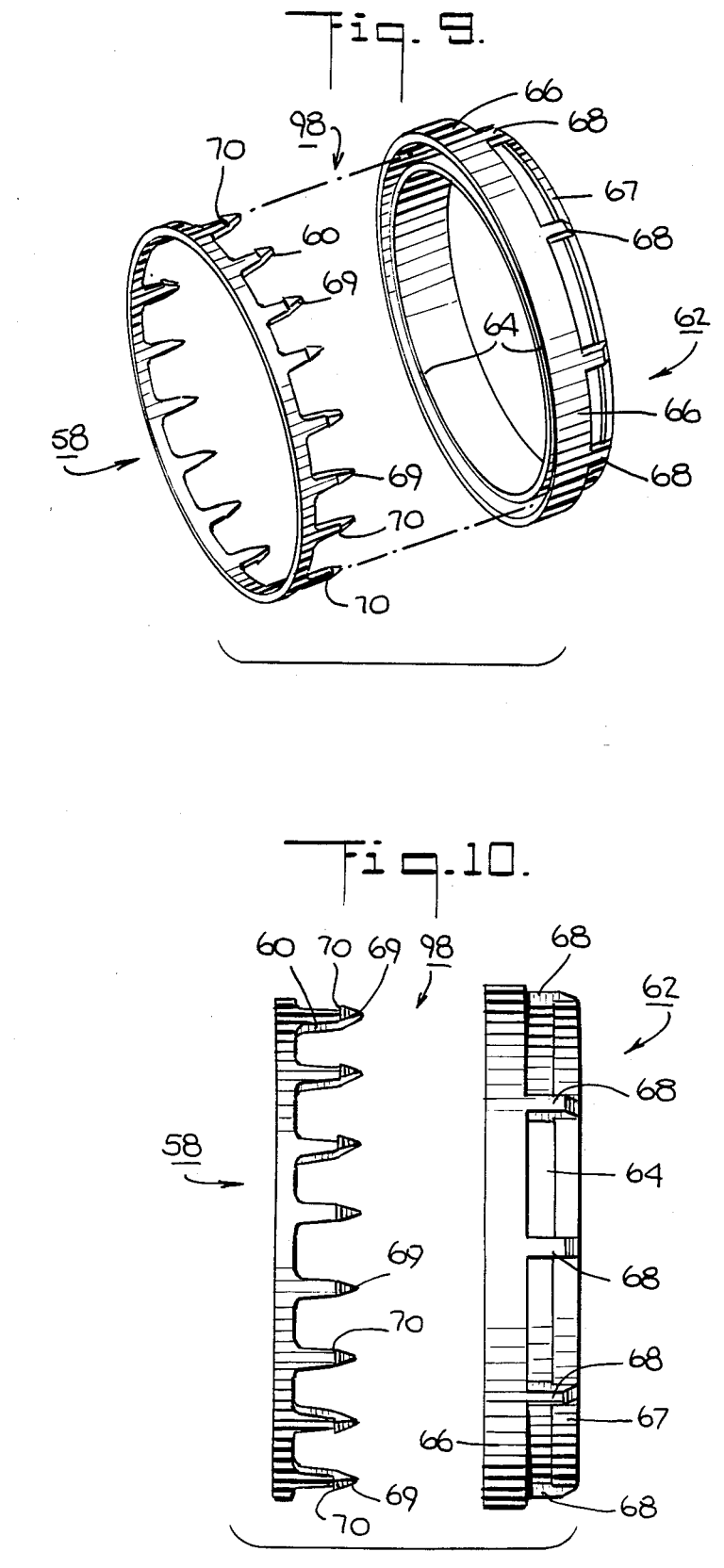

Referring to FIGS. 9 and 10, wherein like reference characters indicate like parts as above, each prong 60 of the stapling part 58 has a sharp tip for piercing tissue while the retaining part 62 is positioned to receive the prongs 60. Catch means are also provided for holding the prongs 60 in the retaining part 62 in order to clamp the pierced tissue therebetween. As illustrated, the catch means includes a radially extending barb 69 on each prong 60 with a proximally facing surface 70 which can be engaged against the retaining ring 66 of the retaining part 62. As indicated, each barb 69 extends radially outwardly of a prong 60 so that the proximally facing surface 70 can be engaged against the retaining ring 66.

The annular stapling part 58 and annular retaining part 62 form a surgical fastening 98 which is of relatively simple construction. Both parts 58, 62 can be rotated relative to the other and need not be precisely registered in order to provide for stapling.

When the two parts 58, 62 are brought together, the prongs 60 pierce the tissue and then enter into the gap between the guide walls 64 and retaining ring 56. At this time, the guide walls 64 and rings 66 temporarily deform due to the wedging action of the barbs 69. After the barbs 69 clear the retaining ring 66, the ring 66 and wall 62 snap back into their normal relationship in which the surfaces 70 of the barbs 69 engage against the retaining ring 66 thus securing the parts 58, 62 together while also clamping the two ends of tissue together. Of note, the flange 67 protects uninvolved tissue from the sharp ends of the prongs 60 (see FIG. 13).

Referring to FIGS. 6 and 12, the anvil assembly 17 also includes an anvil head 81 having an internal conical wall which receives the anvil with the fingers 80 abutting against the wall. In addition, the anvil head 81 has a central shaft 86 about which the hub 82 is mounted via an axial opening 84. The shaft 86 also has an external screw thread 88 on which a hub retainer 92 is threaded via internal screw threads 94. The hub retainer 92 can be threaded into abuttment with the hub 82 with a greater or lesser degree of force. In this way, the anvil head 81 and retainer 92 cooperate to form a means for biasing the fingers 80 of the anvil 18 radially inwardly of the cutting block 76 to permit movement of the fingers 80 radially inwardly in response to removal of the cutting block 76 from the fingers 80. As indicated in FIG. 12, cutting block 76 holds the fingers 80 in a tensioned state. In addition, the fingers 80 are suitably shaped so as to hold the retaining part 62 in a snap fit relation (see FIG. 12). When the cutting block 76 and retaining part 62 are in place, dimensional stability is imparted to the resilient fingers 80.

As indicated in FIG. 12, while the anvil 18 is made of a plastic, the anvil head 81 and retainer ring 92 are made of a metal, such as aluminum. Further, the anvil head 81 is provided with a threaded bore so as to be threaded onto the distal end of the central shaft 14.

Figure 11:
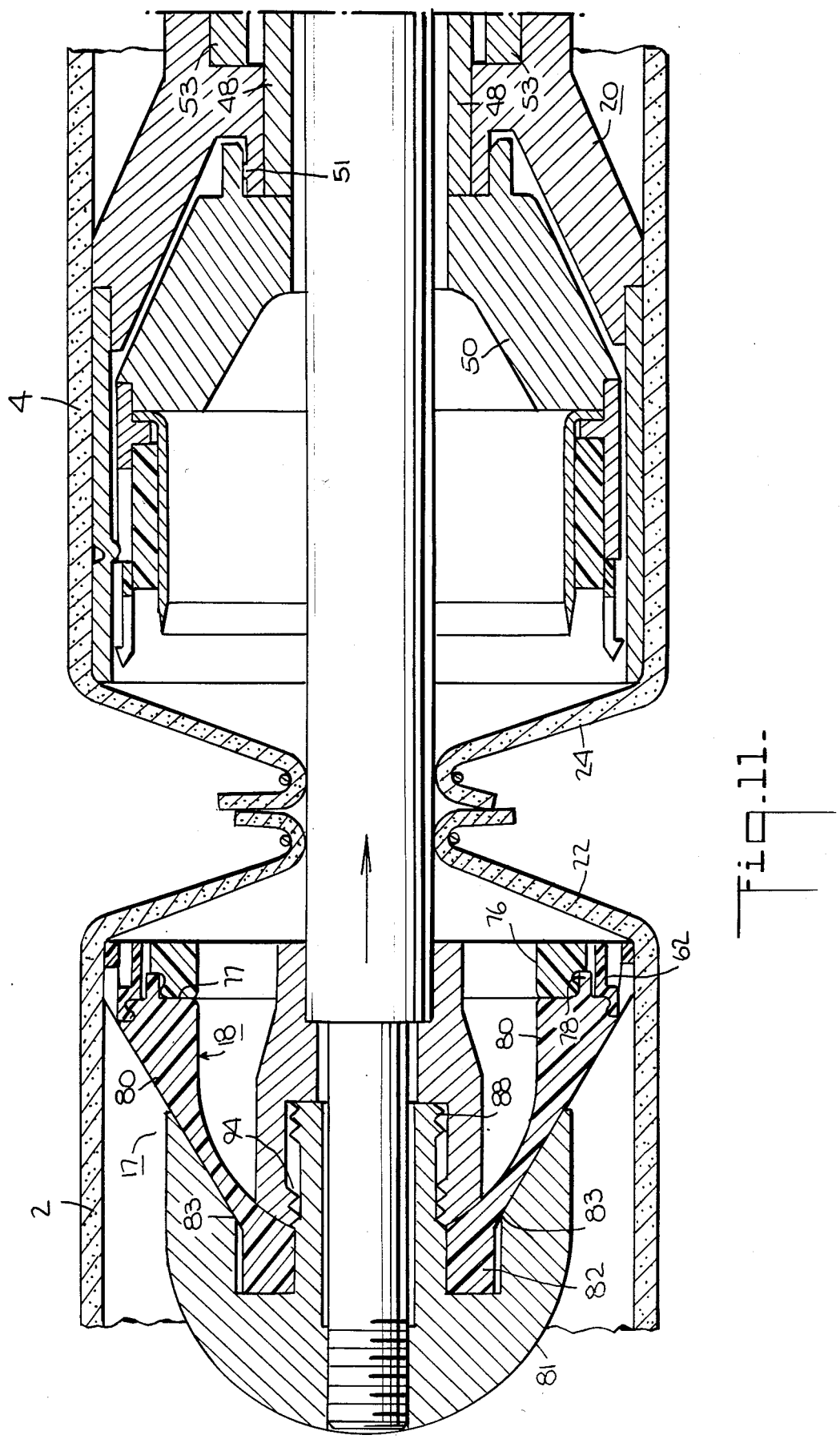
FIG. 11 illustrates a view of the distal end of the surgical stapling apparatus prior to stapling.
Figure 13:
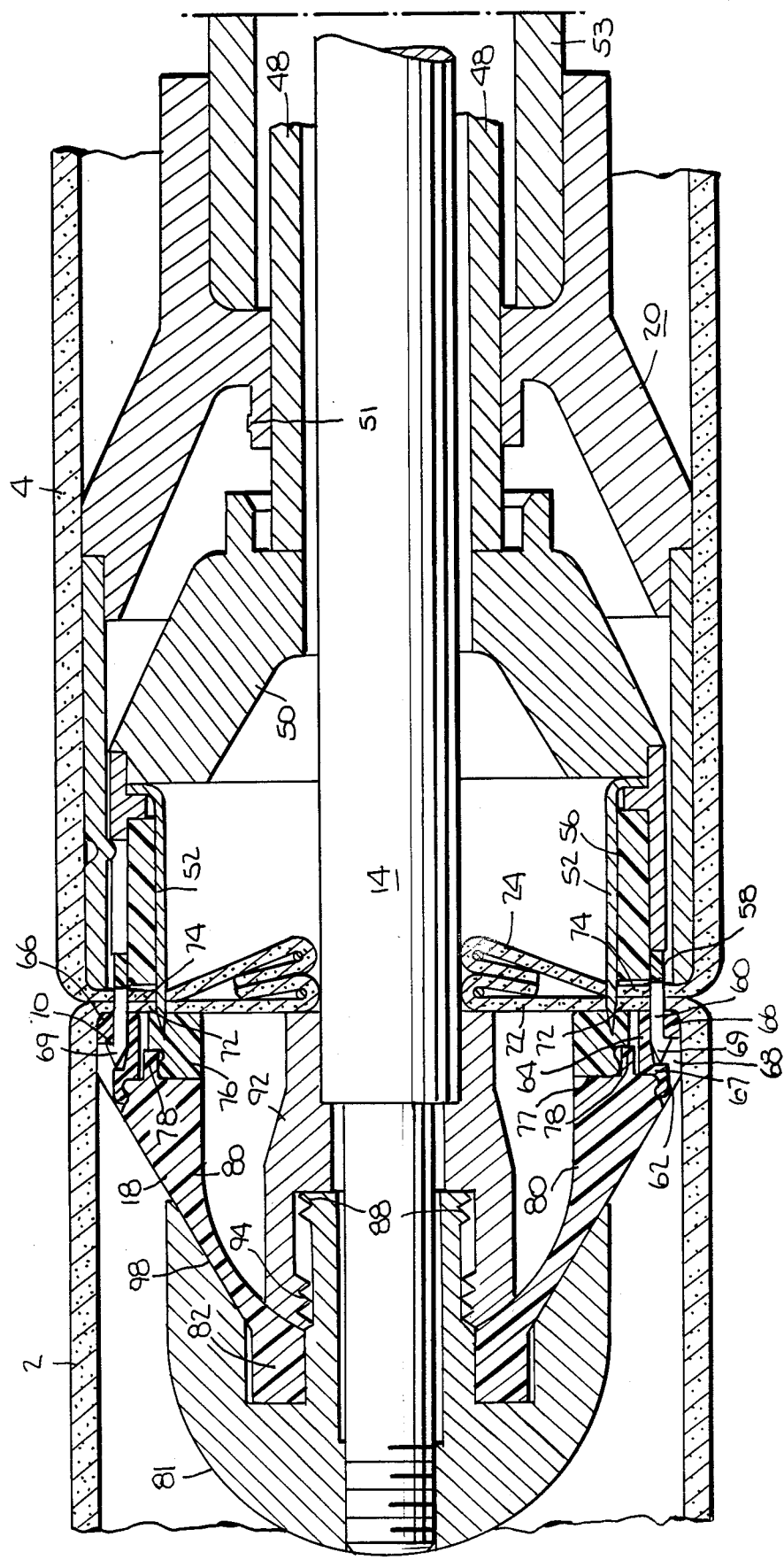
FIG. 13 illustrates a view similar to FIG. 12 of the stapling components after stapling.

Referring to FIG. 11, in use, in order to staple the tubular ends of the tissue together, the stapling apparatus is inserted in a conventional manner. Thereafter, the ends of the tissue 2, 4 are pulled together as indicated in FIG. 11 about the central shaft 14 so as to dispose two areas 22, 24 between the anvil assembly 17 and the fastener holding assembly 20. Thereafter, the shaft 14 is moved proximally via the hand screw 16 so as to move the anvil assembly 17 into a clamped position with the holding assembly 20. In this position, the areas 22, 24 of the tissue 2, 4 are clamped between the anvil 18 and the holding assembly 20. Next, triggering of the instrument via the trigger 28 (see FIG. 1) causes the tube 48 to be moved distally. This in turn moves the actuator 50 distally. As a result, the annular scalpel 52 severs the clamped ends of the tissue on a circular cutting line 99 while penetrating into the cutting block 76. At the same time, the push ring 54 pushes the prong 60 of the stapling part 58 through the clamped ends of the tissue into the annular retaining part 62 with the barb 69 engaging behind the retaining ring 66 as indicated in FIG. 13.

Figure 14:
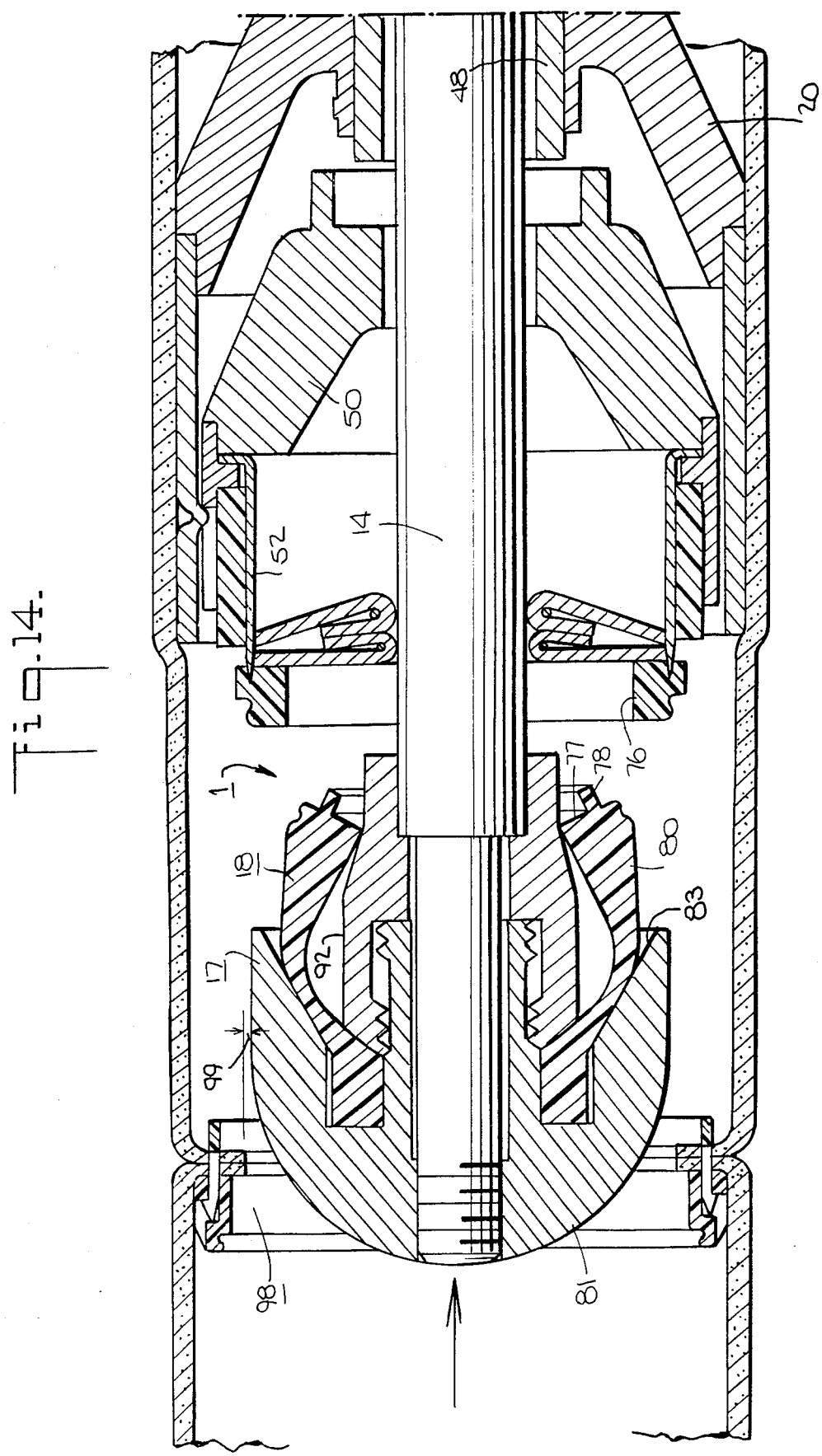
FIG. 14 illustrates a view similar to FIGS. 12 and 13 during withdrawal of the anvil assembly.

Next, the anvil assembly 17 is moved away from the holding assembly 20 by turning of the handscrew 16 (see FIG. 1). During this time, the annular cutting block 76 which has been imbedded by the annular scalpel 52 remains in place on the scalpel 52 as indicated in FIG. 14. At the same time, the annular stapling part 58 remains engaged in the retaining part 62 so as to staple the tissue ends together in a seam as indicated in FIG. 14. In addition, since the cutting block 76 has been withdrawn from the fingers 80 of the anvil 18, these fingers 80 collapse radially inwardly as also indicated in FIG. 14. The degree of collapse of the fingers 80 is such that the fingers 80 fall inside of the cutting line 99 defined by the seamed tissue. Thus, the stapling apparatus 1 may then be removed from within the stapled-together ends. Of note, when the trigger 38 (see FIG. 4) is released, the compression spring 46 biases the slider 44 to return to a proximal position which, in turn, pulls back the shaft 48 into a position as shown in FIG. 14. The actuator 50 remains within the holding assembly 20, for example, as indicated by means of a detent and a holding ring of the holding assembly 20.

The stapling part 58 and retaining part 62 can be made of any suitable materials, such as nylon, polycarbonate or other material. If a non-permanent fastener is to be used, these parts may be made of a tissue absorbable polymer.

Figure 15:
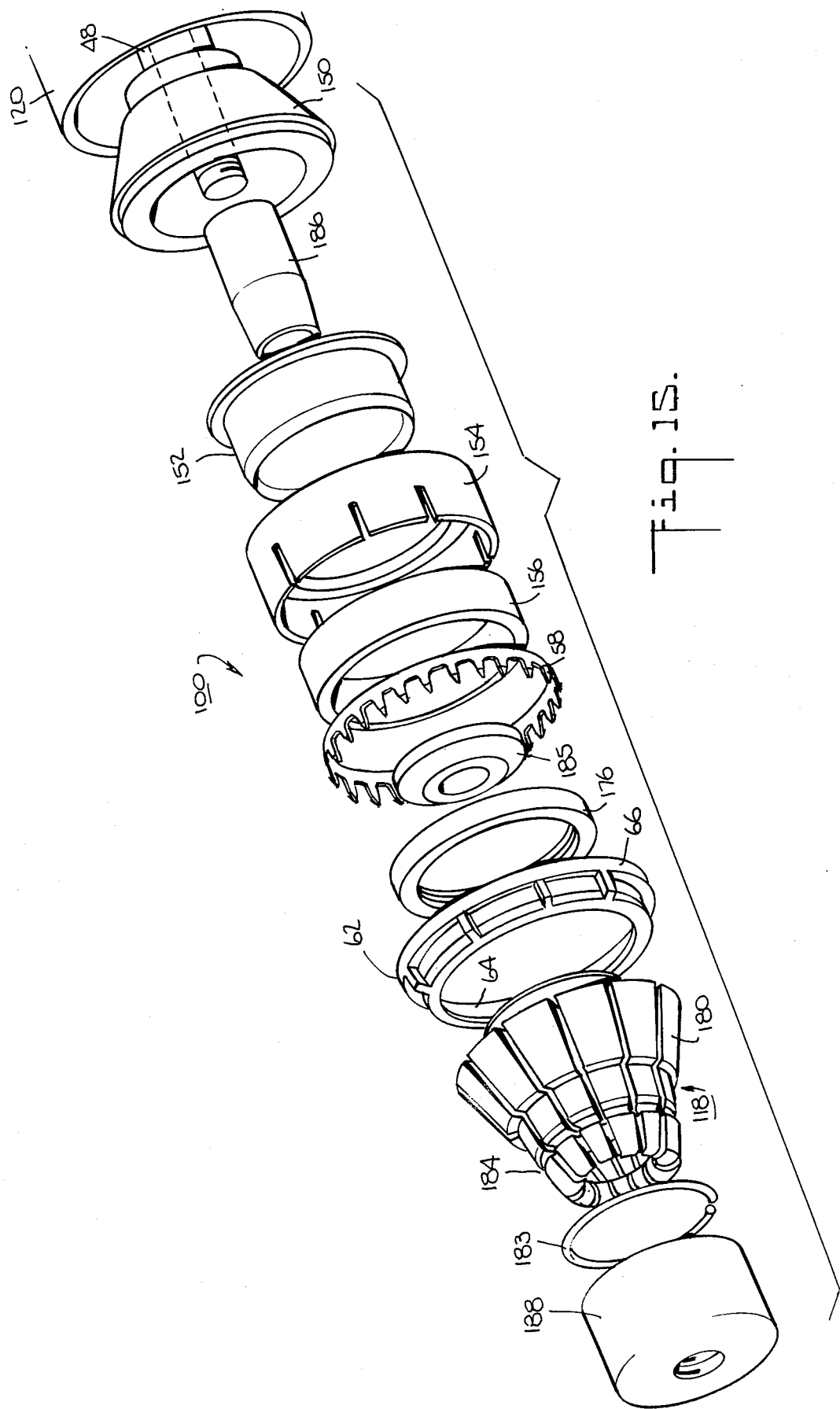
FIG. 15 illustrates an exploded view of the distal end of a surgical apparatus employing a modified anvil assembly in accordance with the assembly.
Figure 16:
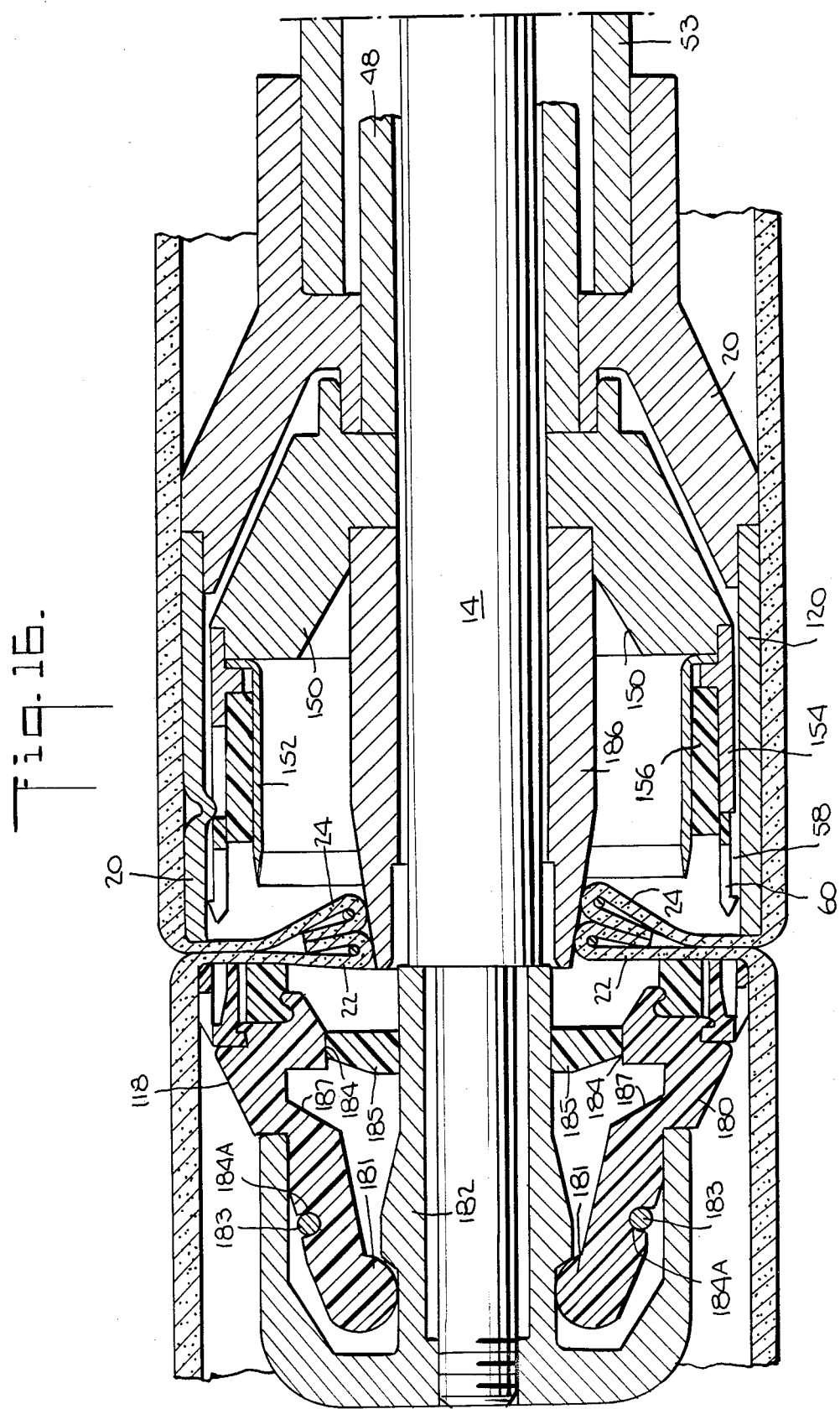
FIG. 16 illustrates a cross sectional view of the distal end of the surgical apparatus employing the anvil assembly of FIG. 15 during a stapling operation.

Referring to FIGS. 15 and 16, wherein like reference characters indicate like points as above, the stapling apparatus may be provided with a modified anvil 118 for the stapling of the surgical fastener parts 58, 62. In this respect, the anvil assembly has an anvil head 188 which is threaded onto a threaded distal end of the shaft 14 and which includes an elongated sleeve 182 with an annular recess defined by the sleeve 182 and the outer periphery of the anvil head 188. As indicated in FIG.

16, the sleeve 182 may be abutted against a shouldered portion of the shaft 14. In addition, a plurality of individual fingers 180 are circumferentially disposed with one end 181 within the recess of the anvil head 188. As shown in FIG. 16, the distal end 181 of each finger 180 rests on a sloped surface on the sleeve 182 while a proximal end rests by way of plane surfaces 184 on the outer surface of an axially movable retainer ring 185 which is mounted on the sleeve 182. In addition, a split circular spring 183 encompasses the fingers 180 and is disposed within a groove 184A in each finger so as to bias the fingers 180 onto the retainer ring 185. Each finger 180 is also provided internally with an intermediately disposed recess 187 which is spaced axially from the ring 185 and which is sized to receive the ring 185 upon axial movement of the ring 185 thereinto to permit inward radial movement of the finger 180 under the bias of the spring 183.

The fingers 180 may be made of plastic, as indicated, or may be made of anodized aluminum or other metals.

The fingers 180 of the anvil 118 are mounted within the anvil head 188 so as to be biased outwardly by the retaining ring 185 against the interior surface of the anvil head 188. The spring 183 which is in the form of a split ring serves to bias the fingers 180 against the retaining ring 185. In this respect, the fingers 180 tend to pivot about the ends 181 (see FIG. 17) within the anvil head 188.

As described above, the anvil 118 carries an annular cutting block 176 and an annular retaining part 62 of the fastener at the proximal end.

Referring to FIG. 16, the actuator of 150 in addition to carrying an annular scalpel 152 and the fastener holding assembly 20 also abuts a pusher 186 in the form of a sleeve at a distal end. As indicated, the sleeve 186 has a recessed distal end to slide over the sleeve 182 of the anvil head 188 in order to abut against the retainer ring 185 when the actuator 150 is moved distally.

Figure 17:
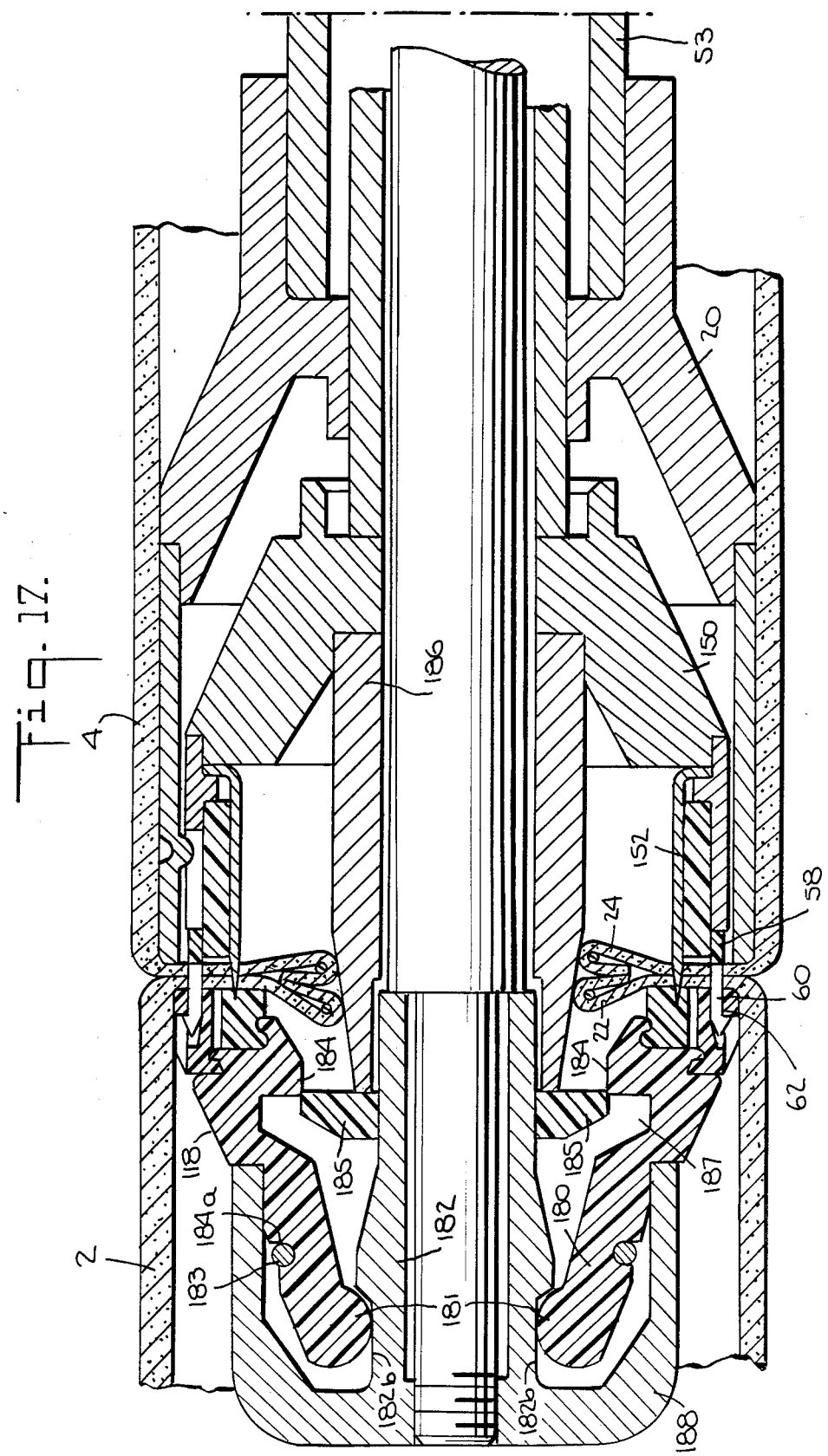
FIG. 17 illustrates a view similar to FIG. 16 of the apparatus after stapling.
Figure 18:
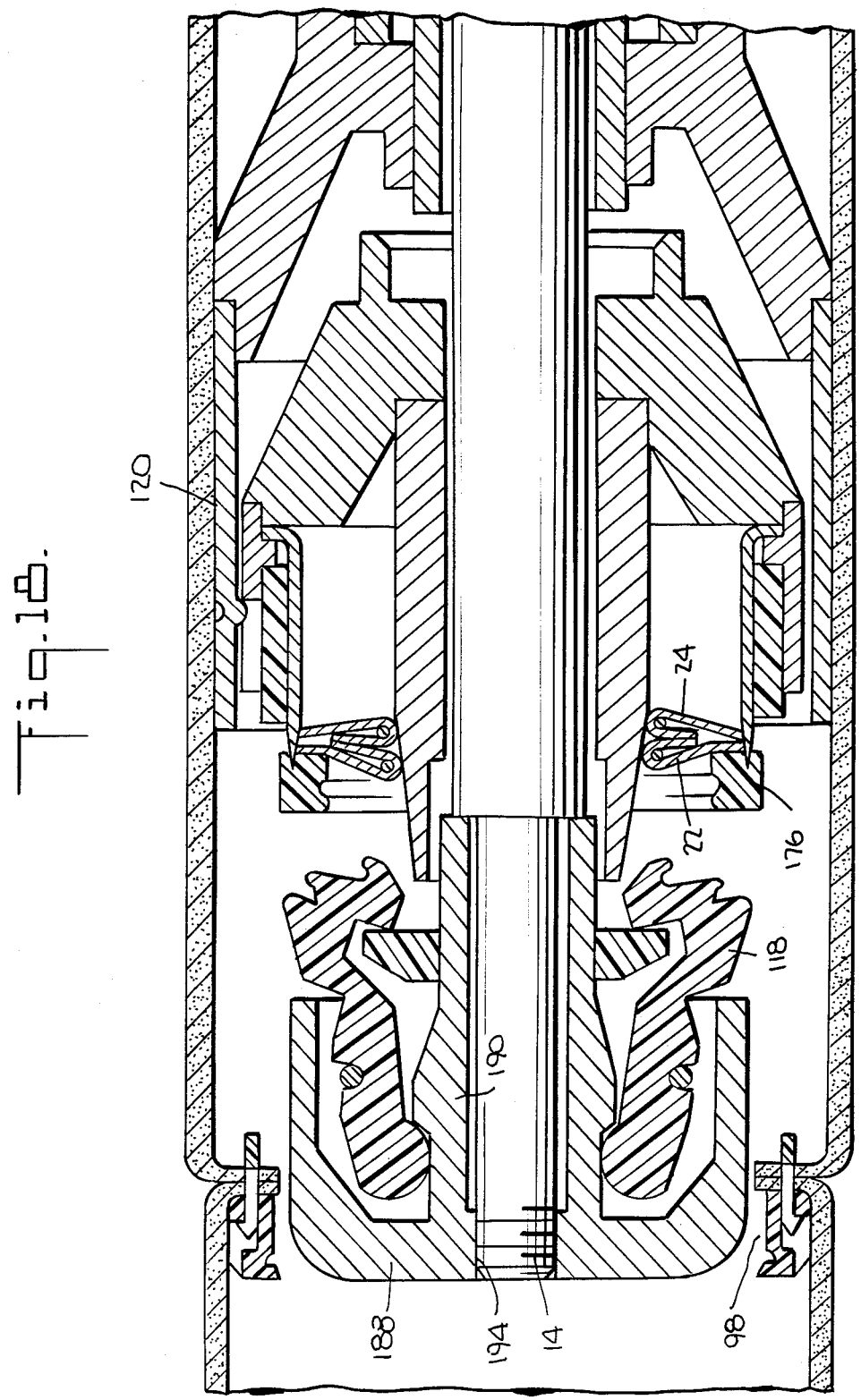
FIG. 18 illustrates a view similar to FIGS. 16 and 17 after collapsing of the anvil assembly in accordance with the invention.

Referring to FIG. 16, 17 and 18, the operation of the stapling apparatus is similar to that as described above. In this respect, after the anvil assembly and anvil head 118 have been drawn towards the fastener holding assembly 20 to clamp the tissue areas 22, 24 therebetween, the trigger (see FIG. 1) is actuated to push the tube 48 and actuator 150 distally. At this time, the pusher 186 slides over the sleeve 182 of the anvil head 188 while the scalpel 152 severs the tissue and penetrates into the cutting block 176 and the prongs 60 of the stapling apparatus 58 pierce the tissue and become retained in the retaining part 62 as indicated in FIG. 17. The motion of the actuator 150 is such that the pusher 186 moves the retainer ring 185 into alignment with the recess 187 of the fingers 180. Thus, the fingers 180 move under the bias of the spring 183 radially inwardly by pivoting about the ends 181.

Thereafter, the apparatus is manipulated as described above to displace the anvil 118 from the holding assembly 120 in order to insure displacement of the anvil 118 from the cutting block 176. At this time, the apparatus can be withdrawn from within the seamed tissue as indicated in FIG. 18. In this respect, the cutting block remains on the scalpel 152 while the fingers 180 are collapsed about the retaining ring 185. At the same time, the sleeve 186 has been moved proximally a slight distance away from the retaining ring 185. In this condition, the outside diameter of the fingers 180 has been reduced so as to pass through the stapled-together tissues.

Of note, the anvil head 188 is sized to be smaller than the fastener 98 and the sleeve 182 is contoured so that the anvil fingers 180 are retained in a snap fit relationship. The invention thus provides a surgical fastener of two-part construction which can be readily manipulated and oriented in place for stapling of body tissue in an anastomosis procedure. Because the fastener parts are annular with the prongs of one part fitting into an annular groove of the other part, precise registration of the prongs relative to the annular gap is not required.

The invention further provides an anvil assembly of relatively simple construction for holding fastener parts in place for stapling purposes while also permitting collapse of the anvil assembly for withdrawal after use. In this respect, the anvil assembly is reduced in outer contour so as to avoid any injury to the seam which has been formed by the surgical fastener.

The invention also provides a surgical stapling apparatus which is relatively simple to use. Further, the apparatus can be readily actuated in a single motion to effect stapling and thereafter, with little effort, be withdrawn from a vessel.

The invention also provides a method of fastening together the ends of two tubular body organs which can be carried out in a relative minimum of time and with relatively minimal effort with respect to previously known techniques.

what is claimed is:

1. An anvil assembly for a surgical fastener comprising
an anvil having a plurality of radiating fingers extending angularly outwardly of a longitudinal axis;
an annular cutting block removably mounted on said fingers for engagement with an annular knife blade; and
means for biasing said fingers radially inwardly of said block to permit movement of said fingers radially inwardly in response to removal of said cutting block from said fingers.

2. An anvil assembly as set forth in claim 1 which further includes a central hub wherein each said finger is integral with said hub and is resiliently deformable.

3. An anvil assembly as set forth in claim 2 wherein said means includes an anvil head having an internal conical wall receiving said anvil with said fingers abutting said wall and a retainer movably mounted within said anvil head and said anvil in abutment with said hub to tension said fingers radially inward.

4. An anvil assembly as set forth in claim 3 wherein said anvil head has a threaded bore for reception of a threaded shaft.

5. An anvil assembly as set forth in claim 1 which further comprises an anvil head having an annular recess receiving one end of each finger, an axially movable retainer ring concentrically within said fingers and mounted on said anvil head; and a circular spring encompassing said fingers within said recess to bias said fingers onto said retainer ring.

6. An anvil assembly as set forth in claim 5 wherein each finger has an intermediately disposed recess spaced axially from said ring and sized to receive said ring upon axial movement of said ring thereinto to permit inward radial movement of said finger.

7. An anvil assembly as set forth in claim 5 wherein each finger is made of aluminum.

8. A surgical stapling apparatus comprising
a central shaft;

an anvil assembly mounted on a distal end of said shaft, said anvil assembly including a plurality of radiating fingers extending angularly outwardly of said shaft, an annular cutting block removably mounted on said fingers and means for biasing said fingers radially inwardly of said block; and a surgical fastener holding assembly mounted on said shaft for relative movement with said anvil assembly to releaseably retain two ends of tubular tissue therebetween, said holding assembly including an annular knife blade coaxially opposite said cutting block for severing tissue disposed therebetween, said blade having an edge for penetrating and holding said block thereon whereby upon movement of said holding assembly and said anvil assembly from each other, said block is removed from said fingers to permit said fingers to move radially inwardly for passage through a stapled seam between the two ends of the tissue.

9. An apparatus as set forth in claim 8 wherein said holding assembly includes a removable annular stapling part having a plurality of coaxial prongs for piercing the tissue and said anvil assembly includes a removable annular retainer part mounted on said fingers about said block for receiving and holding said prongs.

10. An apparatus as set forth in claim. 9 wherein said stapling part and said retaining part include catch means for holding said prongs in said retaining part to clamp the pierced tissue therebetween.

11. An apparatus as set forth in claim 8 wherein said anvil assembly further includes a central hub integrally joining said fingers with said fingers being resiliently deformable.

12. An apparatus as set forth in claim 11 wherein said means for biasing said fingers includes an anvil head threaded on said shaft with an internal conical wall abutting said fingers and a retainer movably mounted on said shaft within said fingers in abutment with said hub to tension said fingers radially inward.

13. An apparatus as set forth in claim 11 wherein said anvil assembly includes an anvil head having an annular recess receiving one end of each finger, an axially movable retainer ring concentrically within said fingers and mounted on said anvil head; and a circular spring encompassing said fingers within said recess to bias said fingers onto said retainer ring.

14. An apparatus as set forth in claim 13 wherein said holding assembly includes a tubular pusher about said shaft for abutting and pushing said retainer inwardly of said anvil assembly and wherein each finger has an intermediately disposed recess spaced axially from said ring and sized to receive said ring.

* * * * *

UNITED STATES PATENT AND TRADEMARK OFFICE
CERTIFICATE OF CORRECTION

PATENT NO. : 4,752,024

DATED : June 21, 1988

INVENTOR(S) : DAVID T. GREEN, et al

It is certified that error appears in the above-identified patent and that said Letters Patent is hereby corrected as shown below:

In the Front page add the following:

Assignee: United States Surgical Corporation
                         Norwalk, CT.

Signed and Sealed this

Tenth Day of January, 1989

Attest:

DONALD J. QUIGG

Attesting Officer         Commissioner of Patents and Trademarks